United States Patent
Wardlaw

[11] Patent Number: 5,888,184
[45] Date of Patent: Mar. 30, 1999

[54] METHOD FOR RAPID MEASUREMENT OF CELL LAYERS

[75] Inventor: Stephen C. Wardlaw, Old Saybrook, Conn.

[73] Assignee: Robert A. Levine, Guilford, Conn.

[21] Appl. No.: 814,535

[22] Filed: Mar. 10, 1997

[51] Int. Cl.[6] ............ G01B 11/06; G01B 21/08; B04B 15/00; G01N 21/00
[52] U.S. Cl. ............ 494/37; 210/86; 210/782; 210/789; 356/381; 494/10
[58] Field of Search .................. 210/782, 789, 210/86; 494/3, 6, 10, 37; 356/39, 40, 344, 381; 422/72; 73/61.69

[56] References Cited

U.S. PATENT DOCUMENTS

| | | | |
|---|---|---|---|
| 3,009,388 | 11/1961 | Polanyi | 494/10 |
| 3,679,367 | 7/1972 | Negersmith et al. | 494/10 |
| 4,027,660 | 6/1977 | Wardlaw et al. | 73/149 |
| 4,156,570 | 5/1979 | Wardlaw | 356/39 |
| 4,409,820 | 10/1983 | Nash | 494/10 |
| 4,558,947 | 12/1985 | Wardlaw | 356/39 |
| 4,567,373 | 1/1986 | O'Meara, Jr. et al. | 250/573 |
| 5,279,150 | 1/1994 | Katzer et al. | 494/10 |
| 5,370,599 | 12/1994 | Marque et al. | 494/10 |

Primary Examiner—John Kim
Attorney, Agent, or Firm—William W. Jones

[57] ABSTRACT

Centrifuged material layer volumes are measured and quantified during centrifugation of the material layers. The material layers are differentially highlighted, preferably by means of one or more fluorescent dyes or stains which are admixed with the sample being analyzed. This kinetic quantification procedure is particularly useful in performing differential blood cell and platelet counts. The blood sample is centrifuged while being subjected to a strobed light source. At least one photometric cell layer compaction measurement is made in conjunction with the light flashes so as to record a degree of cell layer compaction as the sample is being centrifuged. In certain cases, after several successive cell layer compaction readings are derived, a compaction curve is identified and the ultimate degree of cell layer compaction is calculated from the derived compaction curve prior to the achievement of the ultimate degree of cell layer compaction.

8 Claims, 6 Drawing Sheets

METHOD FOR RAPID MEASUREMENT OF CELL LAYERS

TECHNICAL FIELD

This invention relates to a method for rapidly making centrifuged material layer volume measurements. The method of this invention is particularly useful in performing blood constituent count measurements in a centrifuged sample of anticoagulated whole blood.

BACKGROUND ART

The measurement of the blood cell counts in a centrifuged sample of anticoagulated whole blood has been described in the scientific literature, and a method for easily measuring certain blood cell and other constituent layers is described in U.S. Pat. No. 4,027,660, granted Jun. 7, 1977 to Stephen C. Wardlaw et al. In the patented method, a sample of anticoagulated whole blood is centrifuged in a precision capillary tube which contains a plastic float. The float linearly expands some of the cell layers and the platelet layer.

In performing the patented method, the blood sample is centrifuged for about five minutes at about 12,000 RPM, and then the expanded lengths of the cell and platelet layers are measured. One of the problems in the patented method pertains to the relatively high centrifuge RPM required to reliably compact the layers, particularly the platelet layer. If the constituent layers are not completely or uniformly packed, the results derived by the method may be inaccurate. The aforesaid high RPM centrifugation requires an expensive centrifuge, and increases the risk of tube breakage. Another problem relates to the required minimum five minute centrifugation time period, which is undesirable in many medical situations. Still another problem relates to the need for the operator to remove the tube from the centrifuge and re-insert it into a reader. Because this operation must be performed within a limited time interval following centrifugation, it requires the close attendance of the operator, which is inefficient and further exposes the operator to a potentially hazardous sample.

It would be desirable to be able to measure the blood constituent layers in a shorter period of time, and with a lower RPM centrifuge, and/or to reduce the amount of sample tube handling.

DISCLOSURE OF THE INVENTION

This invention relates to an assembly for quickly determining individual material volume measurements during centrifugation of a gravimetrically separable material mixture sample, such as an anticoagulated whole blood sample. Additionally, this invention relates to a method which can determine blood constituent volume measurements, and blood constituent counts during centrifugation of an anticoagulated whole blood sample before the centrifugation step is finished. The method of this invention utilizes a combined centrifuge and reader which will perform the functions of both centrifugation and reading, and thus simplify the performance of the material layer measurements described in the aforesaid U.S. patents. The method of this invention provides a kinetic analysis of blood cell compaction. By following the principles of this invention, white blood cell and platelet layers can be quantified in a relatively low RPM centrifuge, for example a centrifuge which operates at speeds of between about 8,000 to about 10,000 RPM, although the higher speed 12,000 RPM centrifuge can also be used.

During the process of gravimetrically forming cell layers in a centrifuged anticoagulated whole blood sample there are two counteractive forces at work, i.e., outward compaction of the cells and other formed components in the sample; and inward percolation of the plasma in the sample. As the cells and other formed component layers in the blood sample settle during centrifugation, the layers compact thereby decreasing the length of the layers. At the same time, the fluid (plasma) component of the blood sample percolates through the compacting layers.

For cell compaction to occur, the fluid component must be displaced, but as the cell layers continue to compact the percolation paths for the fluid become more tortuous. Cell layer compaction will initially progress rapidly but will become increasingly slower as compaction increases and percolation becomes more difficult. Thus the rate of compaction is non-linear. Since the rate of compaction varies considerably between different blood samples due to fluid viscosity and/or other factors, a single reading of a cell layer which is taken prior to complete compaction of the cell layer cannot be extrapolated to predict the extent of the final cell layer compaction. Therefore the thickness (or length) of the fully compacted cell layer cannot be determined from a single measurement of the thickness (or length) of a cell layer which reading is taken during the centrifugation step. This fact has formed the basis of the traditional method of determining the optimum centrifuge speed, and time, so that measurements of the cell layers' thickness will be made only after the cell layers would be expected to show no further compaction. This "complete compaction" centrifugation time is considered deemed to be the minimum time required before measuring any centrifuged anticoagulated whole blood constituent layers.

I have discovered that the inherent unpredictability of the extent of final blood cell layer compaction can be overcome by making several separate preliminary measurements of the cell layers' thickness during the ongoing centrifugation step, and then fitting the derived data to a non-linear mathematical algorithm that will predict the fully compacted cell layer thickness. This procedure does not require ultimate layer compaction, and in fact, the fully compacted cell layer thickness may be mathematically predicted after only four or five preliminary cell layer thickness measurements. Additionally, the method of this invention allows for an accurate calculation of the ultimate extent of blood cell layer compaction, and therefore the thickness of a fully compacted cell layer, over a wide range of centrifuge speeds. Thus a plurality of cell layer thickness measurements that are taken during the low speed centrifugation of an anticoagulated whole blood sample can accurately predict the ultimate degree of cell layer compaction which will result from a prolonged centrifugation step that is performed at a much higher centrifuge speed, such as is required by the prior art.

The method of this invention involves the use of: a centrifuge; a fluorescent colorant excitation light source; a photodetector; and a microprocessor controller for controlling operation of the assembly, and for collecting data from readings taken by the assembly. The light source is preferentially a pulsating light source which periodically illuminates the blood sample in the sampling tube as the latter is being centrifuged. Illumination of the blood sample in the tube causes fluorescence of certain of the blood cell constituents as well as illumination of the red blood cell layer, so that the photodetector can discriminate between the various cell layers in the tube that are gravimetrically compacted during the centrifugation step. By selection of the appropriate filters on both the light source and the detector, the light reflected from the material layers can be measured, as well as the fluorescence. Also, if a light source is positioned in opposition to the detector, or if a reflective surface is provided behind the capillary tube, the light transmitted through the capillary tube can be measured as well. The pulsing of the light source is synchronized with the position of the tube during centrifugation, so that the tube will be illuminated as it passes by the photodetector. The optics and filters used in performing the method of this invention are generally similar to those described in U.S. Pat. No. 4,558,947, granted Dec. 17, 1985 to S. C. Wardlaw, the disclosure of which patent is incorporated herein in its entirety.

If the sample is analyzed by the aforesaid kinetic technique, the extent of compaction of the several blood sample constituent layers is periodically imaged during centrifugation, and the sequential constituent layer images are stored in the microprocessor controller in the assembly. After a sufficient number of images have been obtained and stored, about four or five for example, the microprocessor controller will be able to calculate the degree of ultimate compaction of the constituent layer or layers being measured, and will display the calculated value. At that point, centrifugation of the sample will be terminated. The microprocessor controller controls operation of the assembly in that, on command, it will: initiate centrifugation; monitor the RPM of the centrifuge; synchronize the light pulses with the ongoing centrifuge RPM; control operation of the photodetector; receive and store constituent layer readings; calculate the ultimate degree of constituent layer compaction, and the resultant constituent counts or values; and shut the centrifuge down. The operator thus need only place the blood sampling tube in the centrifuge, and initiate operation of the assembly. For operator convenience and safety, the blood sampling tube can be contained in a special cassette of the general type described in U.S. Pat. No. 5,776,078, issued Jul. 7, 1998.

If, on the other hand, the object is to measure the final extent of cell compaction following a fixed period of centrifugation, the layer lengths may be analyzed by the taking of one or more images following the fixed period centrifugation while the centrifuge continues spinning. Thus the advantage of being able to measure the extent of cell layer compaction without having to transfer the blood sample tube from the centrifuge to a separate reader instrument is realized.

It is therefore an object of this invention to provide a method for deriving an ultimate material layer thickness measurement in a centrifuged material mixture prior to the actual achievement of the ultimate layer thickness.

It is another object of this invention to provide a method which will allow the reading of the material layer thicknesses following a fixed period of centrifugation while the sample is still within the centrifuge.

It is a further object of this invention to provide a method of the character described wherein the material mixture is an anticoagulated sample of whole blood.

It is an additional object of this invention to provide a method of the character described wherein a plurality of preliminary sequential layer interface locations are sensed and stored during centrifugation of the mixture, with the interface data obtained being used to calculate the ultimate layer thickness.

It is a further object of this invention to provide a method of the character described wherein the ultimate thickness of a plurality of material layers in the sample being centrifuged can be derived from preliminary layer thickness measurements.

These and other objects and advantages of the invention will become more readily apparent from the following detailed description of the invention when taken in conjunction with the accompanying drawings, in which:

DETAILED EXAMPLE FOR CARRYING OUT THE INVENTION

Figure 1:
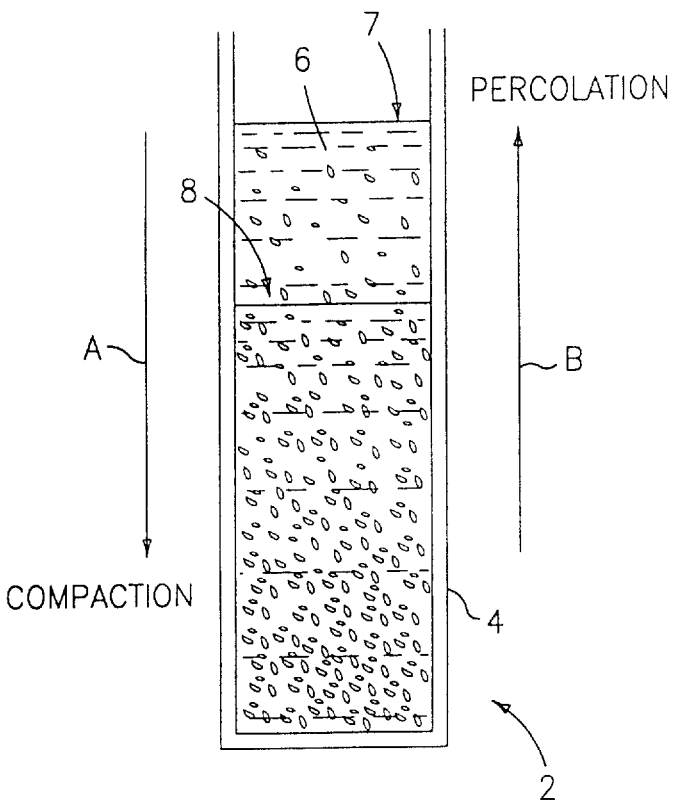
FIG. 1 is a schematic view of a tube containing a material mixture sample as the latter is being centrifuged in the tube.

Referring now to FIG. 1, there is shown a schematic view of a tube 2 having a transparent side wall 4 and closed at the bottom. The tube 2 is filled with a mixture of a particulate material component suspended in a liquid component 6. FIG. 1 illustrates the dynamics of particulate compaction and liquid percolation, as indicated by arrows A and B respectively, both of which occur during centrifugation of the particulate component/liquid component mixture. As centrifugation progresses, the particulate component will gravimetrically separate from the liquid component 6, and will, at some point in time, form an interface 8. The interface 8 continually gravitates away from the upper surface 7 of the liquid component 6 as centrifugation continues. It will be understood that more than one interface 8 may form in the sample being centrifuged, depending on the nature of the sample.

Figure 2:
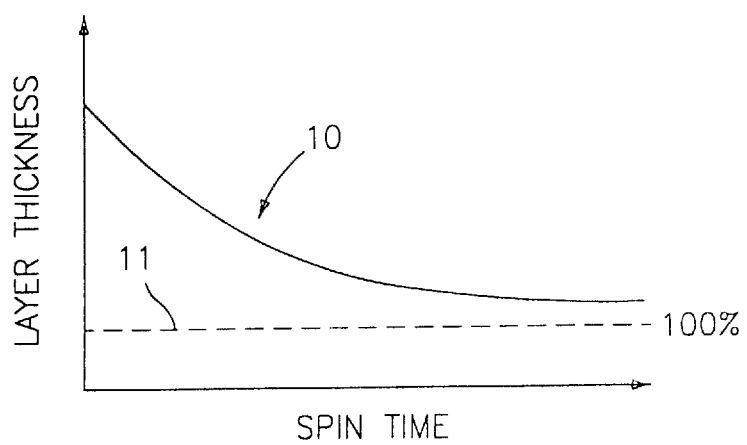
FIG. 2 is a plot of the dynamics of layer compaction during centrifugation of the material mixture, with the layer thickness being plotted against elapsed centrifugation times.

I have discovered that when the position of the particulate component/liquid, or component/component interfaces 8 are monitored over the course of time, the sequential positions of the interfaces define a function curve 10 of the general type depicted in FIG. 2, wherein the initial change in interface position is relatively rapid, but slows appreciably as particulate component compaction progresses. At some point in time, particulate component compaction ceases, and the particulate component-liquid component separation is complete. In the context of this invention, I refer to this cessation of particulate component compaction as "ultimate" compaction which is represented by the dotted line 11 in FIG. 2.

It will be noted that the same phenomenon occurs when a complex mixture of particulate components suspended in a liquid, such as anticoagulated whole blood, is centrifuged. In this case a plurality of particulate component layers will form gravimetrically, with the liquid component 6 percolating to the top of the centrifuge tube 2. Blood is an example of such a complex mixture of particulate components, since the red blood cells are heavier than the granulocytes, lymphocytes, monocytes and platelets, in order of decreasing density, and since all of the cells in a blood sample are heavier than the plasma component of the blood sample. When an anticoagulated sample of whole blood is centrifuged the various cell/cell and cell/plasma interfaces will gravitate through the blood sample in the same general manner as is illustrated by FIG. 2. It should be noted that in a complex mixture of materials, such as whole blood, under some circumstances middle layers may actually increase in thickness rather than compact. This may occur when the separation of a target component from the mixture exceeds the compaction rate of that layer. In all cases, however, the mathematical analysis and extrapolation is performed identically to, and has the same effect as that done on the layers which decrease in thickness.

The curve described by the rate of change of the location of any particulate constituent interface, and therefore constituent layer thicknesses in a sample undergoing centrifugation is essentially an hyperbola. This fact can be used to mathematically predict the ultimate extent of particulate constituent layer compaction, and therefore the ultimate layer thicknesses and layer volumes of the particulate constituent layer or layers in the centrifuged sample.

It should be noted that the compaction of the cell layers may not immediately follow a hyperbolic function starting at time zero. To determine when the movement of the interface has reached the point where it follows a hyperbolic function and the ultimate compaction may therefore be calculated, it is only necessary to periodically monitor the interface position or layer thickness and calculate successive slope measurements as $S=dP/(1/t)$, where: S is the slope of the change; dP is the change in interface position (or layer thickness); and t is the elapsed time since the start of centrifugation. When successive values of S no longer change, subsequent preliminary data points may then be collected and the ultimate layer compaction can be determined.

Figure 3:
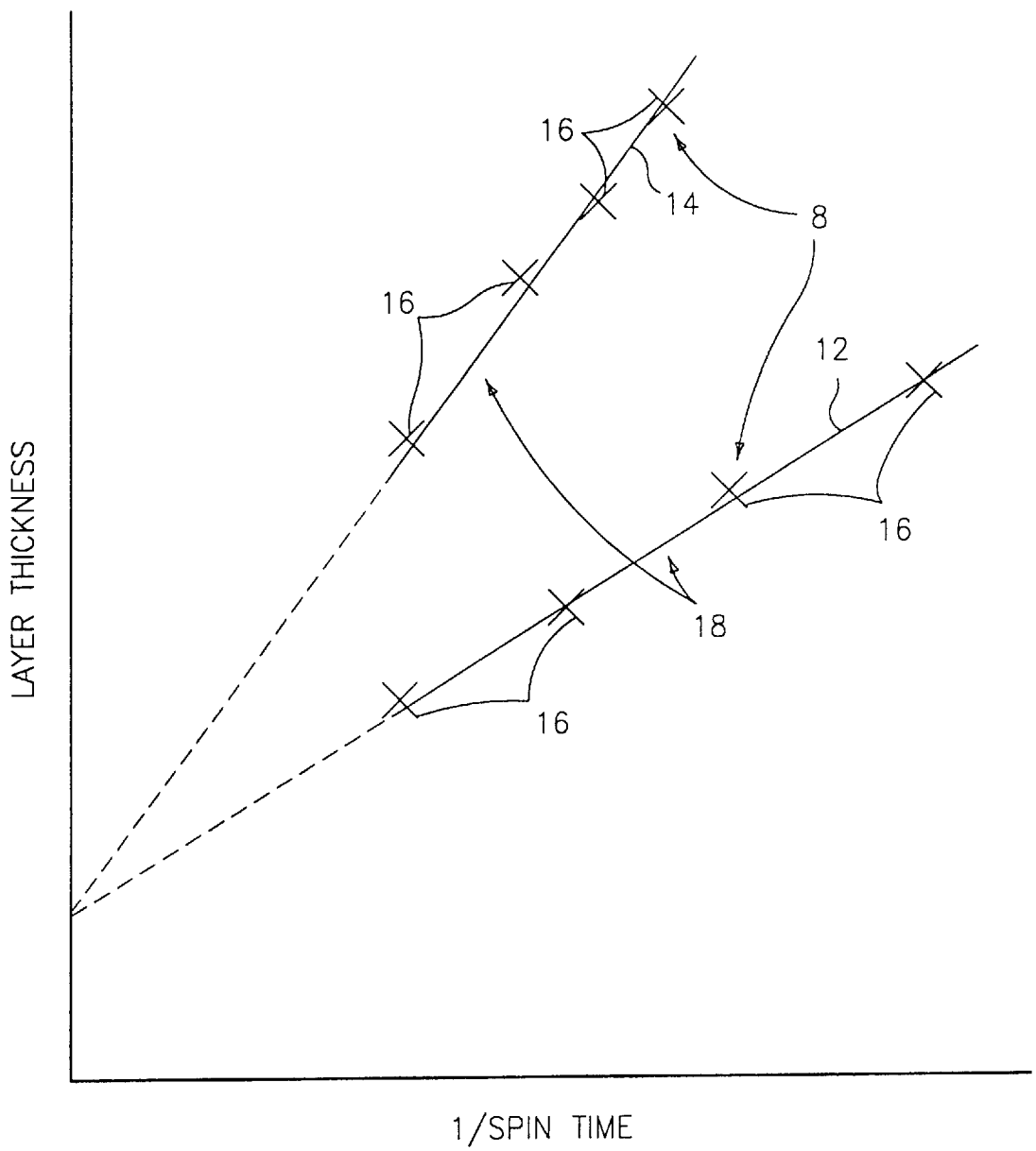
FIG. 3 is a graph showing how an ultimate platelet layer height was calculated in a specific case when a blood sample was centrifuged at two different speeds, with platelet layer being plotted against the reciprocal of elapsed centrifugation times.

FIG. 3 shows a specific example of the same anticoagulated whole blood sample centrifuged at two different speeds, wherein the slopes of the hyperbolic curves as shown in FIG. 2, are linearized by plotting the reciprocal of successive elapsed centrifugation times against successive measured thicknesses of the compacted platelet layer interfaces 8 at two different centrifuge speeds, i.e., at 8,000 RPM and 12,000 RPM. The line 14 generally denotes the rate of change in the platelet layer thickness during centrifugation of the test samples in a high speed of 12,000 RPM centrifuge; and the line 12 generally denotes the rate of change in the platelet layer thickness during centrifugation of the test samples in a lower speed of 8,000 RPM centrifuge, the latter of which provides only 40% of the G-force of the former.

In order to determine the rate of change slopes, a series of preliminary successive platelet layer thicknesses 16 are measured, and least-squares fits are calculated thereby giving the best path 18 amongst the preliminary layer thickness data points 16. To calculate the ultimate compacted layer thickness, the regression function is extrapolated to an ultimate spin time, in this case infinity, where the value of the reciprocal of the elapsed centrifuge time is zero. The intercept of the rate of change of layer thickness plot at that point on the Y axis identifies the ultimate compacted layer thickness. It is noted that although the centrifuge speeds are considerably different, the end result is the same; and that readings need be taken for only a relatively short period of time, such as for two to three minutes as compared to five to ten minutes, required by the prior art. The preliminary measurements may be taken while the centrifuge continues to spin.

Figure 4:
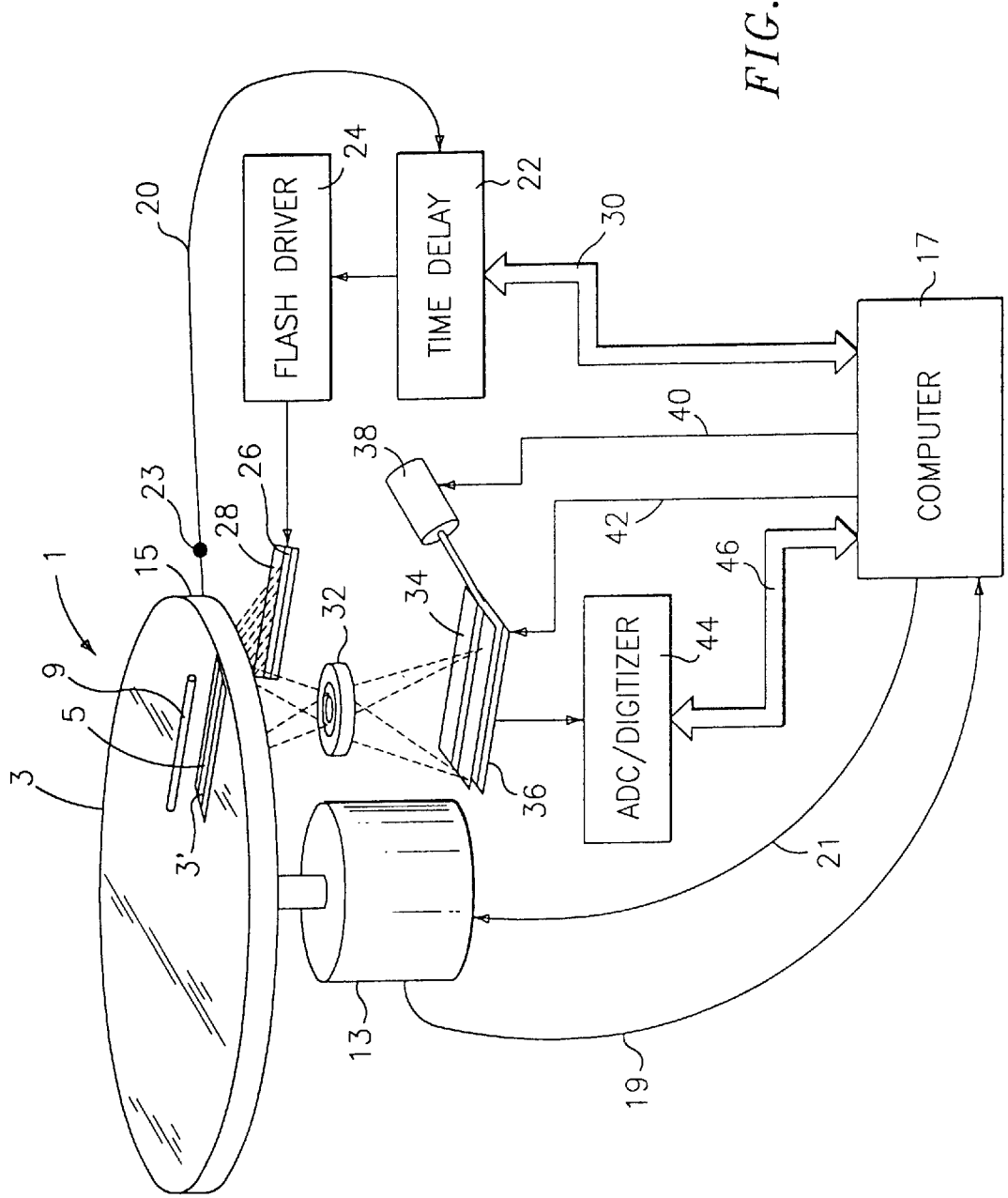
FIG. 4 is a schematic perspective view of a blood sample measurement assembly used in performing the method of this invention.

Referring now to FIG. 4, there is shown a schematic view of a combined centrifuge and reader assembly, which is indicated generally by the numeral 1. The assembly 1 includes a centrifuge platen 3 which includes a recess 5 for holding a transparent capillary tube 9. The tube 9 may be placed directly in the recess 5, or the capillary tube 9 may be held in a cassette (not shown) of the type disclosed in U.S. Pat. No. 5,776,078. In any event, at least one surface of the tube 9 must be optically visualized for the purpose of collecting the desired optical information from the tube contents. The centrifuge platen 3 is rotationally driven by a motor 13, which is controlled by output line 21 from an assembly microprocessor controller 17. The rotational speed of the motor 13 is monitored by the controller 17 via line 19 thereby allowing the controller 17 to regulate the speed of the motor 13 and thus the centrifuge platen 3. When the centrifuge platen 3 reaches its predetermined operating speed, which may be between about 8,000 and 12,000 RPM, the action of the controller 17 will depend upon the type of analysis required. If it is desired to read the material layer compaction following a fixed period of centrifugation, the controller 17 will energize the motor 13 for a desired fixed period of time and the layer compaction reading will be taken thereafter while the centrifuge continues to spin.

On the other hand, if it is desired to kinetically measure the material layer compaction, multiple sequential readings of the gravitationally compacting blood cell layer heights in the tube 9 are taken. As the platen 3 rotates, an indexing device 15 on the side of the platen 3 passes by and interacts with a sensor 23 which sends a signal through line 20 to a programmable delay 22. The indexing device 15 can be a permanent magnet and the sensor 23 can be a Hall-effect sensor. Alternatively, the indexing device 15 could be a reflective member on the edge of the platen 3, and the sensor 23 could be an infrared emitter-receiver pair. Still another alternative sensing device could include a sensor in the driving motor 13 provided that the platen 3 were rigidly affixed to the shaft of the driving motor 13.

After a predetermined time has elapsed from the receipt by the controller 17 of a signal from the proximity sensor 23, a flash driver 24 triggers a flash tube 26 that delivers a brief pulse of light, preferably less than about fifty microseconds in duration. A filter and lens assembly 28 focuses the light of the desired wavelength from the flash tube 26 onto the tube 9. When the flash tube 26 is positioned beneath the platen 3, the latter will include an opening 3' between the sample tube 9 and the flash tube 26 and filter and lens assembly 26. Due to the fact that the exact rotational rotational speed of the platen 3 is monitored by the controller 17 via line 19, and since the circumferential distance between the position of the index 15 and the position of the tube 9 is fixed, the required time delay for timely energizing the flash tube 26 can be determined by the controller 17 and expressed through data bus 30 so as to control operation of the flash driver 24.

When the tube 9 is illuminated by the flash tube 26, the light reflected by the cell layers, or light from fluorescence of the cell layers, is focused by a lens assembly 32 through a light filter set 34 onto a linear image dissector 36, which is preferably a charge-coupled device (CCD) having at least 256 elements and preferably 5,000 elements so as to achieve optimum optical resolution. Light of an appropriate wave length can be selected by an actuator 38 such as a solenoid or stepping motor and which is controlled by the controller 17 via line 40 whereby the actuator 38 can provide the appropriate filter from the filter set 34, depending upon the light wavelength selected by the controller 17. Alternatively, electrically variable filters could be used to provide the proper light wavelengths, or CCDs with multiple sensors, each with its own particular filter could be used. Suitable electrically variable filters can be obtained from Cambridge Research and Instrumentation, Inc. of Cambridge, Mass. Suitable CCD's are available from Sony, Hitachi and others, and are common instrumentation components.

Just prior to receiving the light flash from the flash tube 26, the electronic shutter in the CCD 36 is opened by the controller 17, via line 42. Immediately following the flash, the data from the CCD 36 is read into a digitizer 44 which converts the analog signals from each of the CCD cells into a digital signal. The digitized data is then transferred to the controller 17 through a data bus 46 so that the data can be immediately analyzed or stored for future examination in the controller 17. Thus at any desired point during the centrifugation process, optical information from the sample tube 9 can be collected and analyzed by use of the assembly described in co-pending U.S. patent application Ser. No. 08/814,536, filed Mar. 10, 1997. The mathematical calculations described above which are use to derive "ultimate compaction" can be made by the controller 17.

Figure 5:
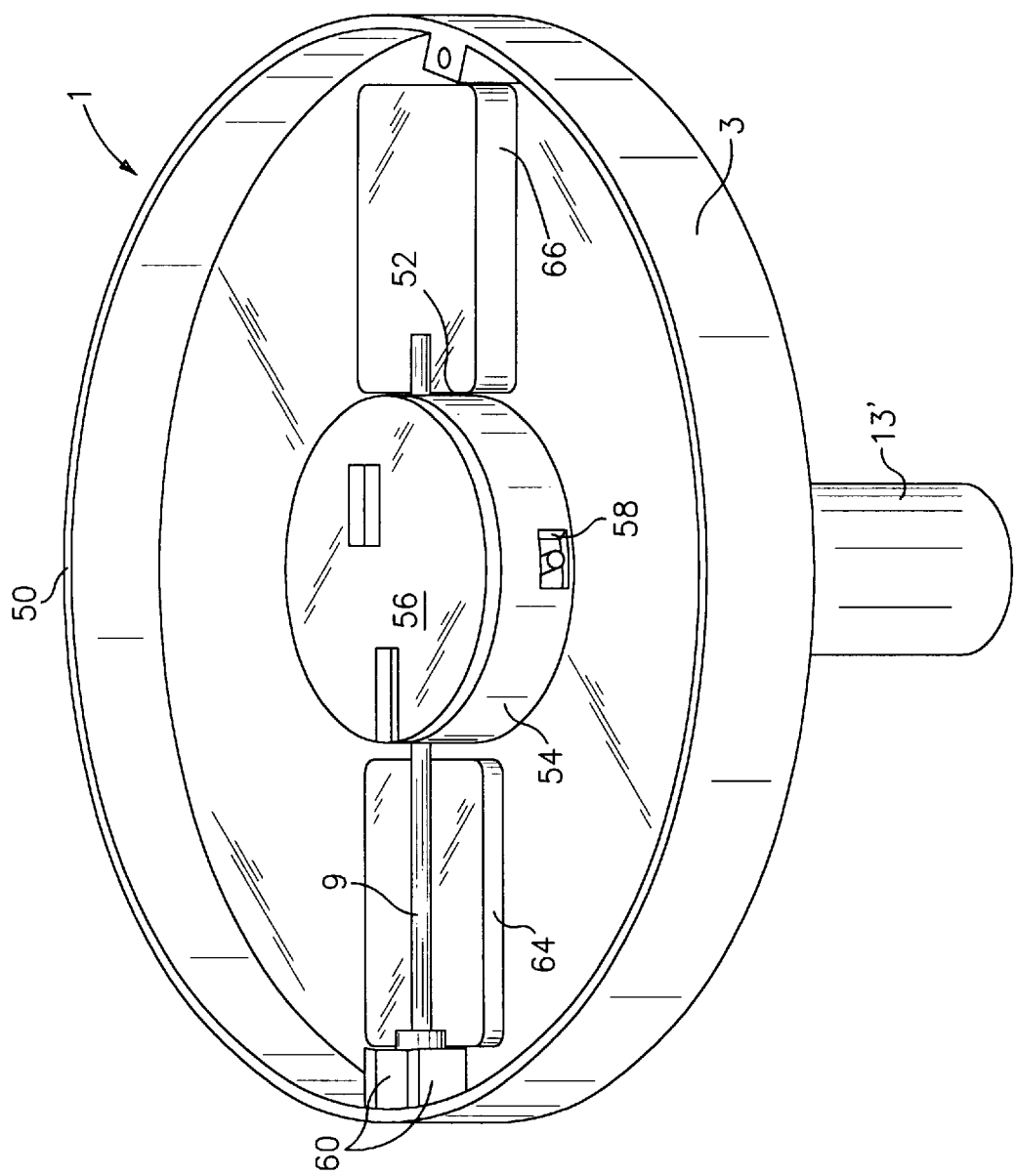
FIG. 5 is a perspective view of a preferred embodiment of a centrifuge platen and drive mechanism designed for use in connection with this invention.

Referring now to FIG. 5, there is shown a preferred embodiment of a centrifuge platen assembly 3 which is designed for use when the flashing light source 26 and the digitizer 44, which are shown in FIG. 4, are positioned above or below the platen 3. The platen 3 is generally dish-shaped and includes an outer rim 50 and a basal floor 52. A central hub 54 is secured to the platen floor 52, and the hub 54 is closed by a cover 56. The hub 54 has a pair of diametrically opposed windows 58 formed therein. The sample tube 9 is mounted on the platen 3. One end of the tube 9 is inserted into an opening in the hub 54, and the other end of the tube 9 is lowered into a slot 60 formed in a block 62 that is mounted on the platen rim 50. The platen floor 52 is provided with an opening (not shown) covered by transparent plate 64. A counterweight 66 is diametrically disposed opposite the plate 64 so as to dynamically balance the platen 3. The plate 64 allows the platen 3 to be used with light sources and detectors which are located either above or below the platen floor 52. They also allow the assembly 1 to utilize either reflected light, fluorescent emission or transmitted light in connection with the sample to achieve the desired results. The specific example shown in FIGS. 5 and 6 uses a single tube; however, multiple tubes can also be analyzed by the assembly 1 by mounting a sample tube in a diametrically opposed position on the platen 3, and by altering the timing from the index to the flash so as to provide readings for each separate tube. The drive shaft of the earlier described centrifuge motor 13 is designated by the numeral 13'.

Figure 6:
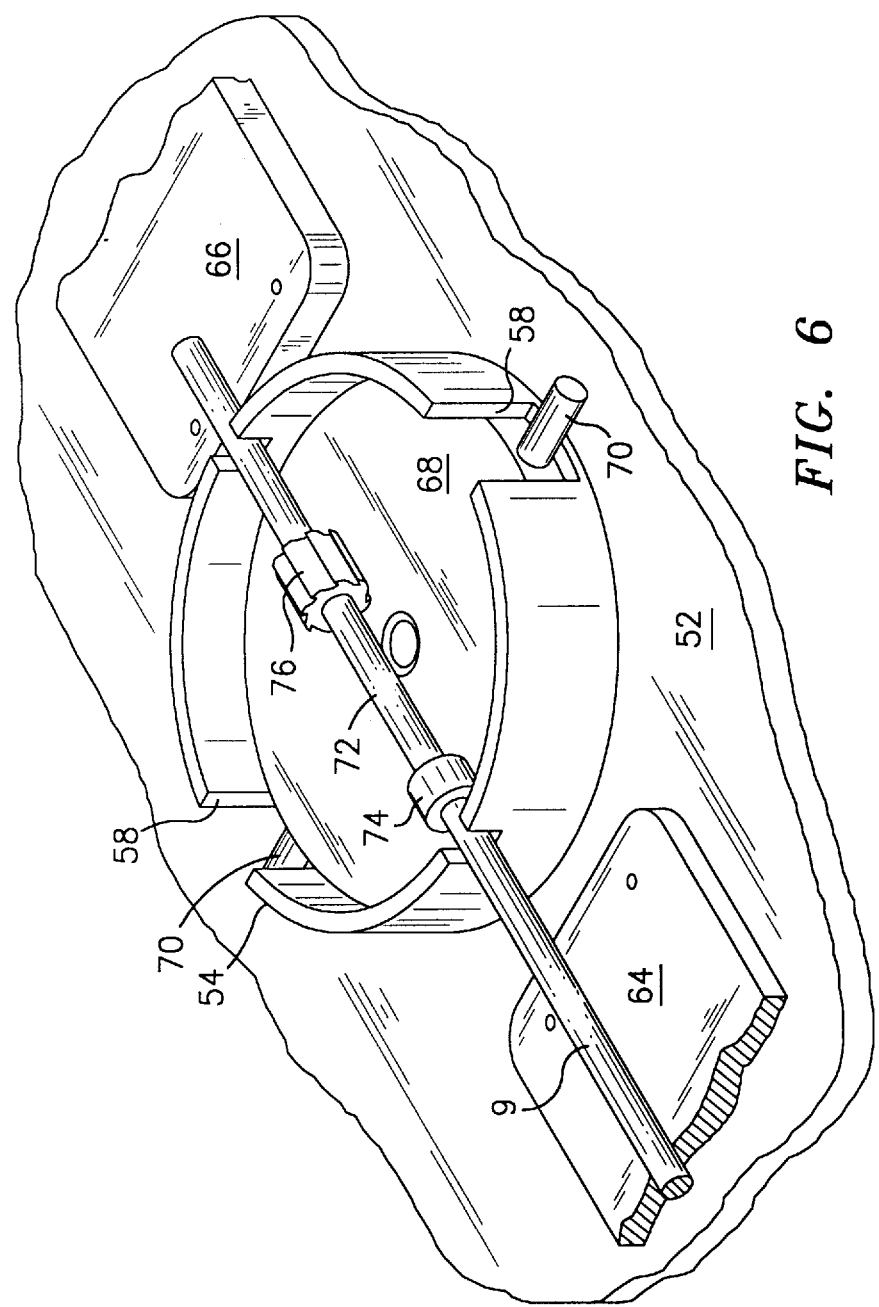
FIG. 6 is a fragmented perspective view of a tube holder and tube rotating mechanisms which are utilized in performing the method of this invention.
Figure 7:
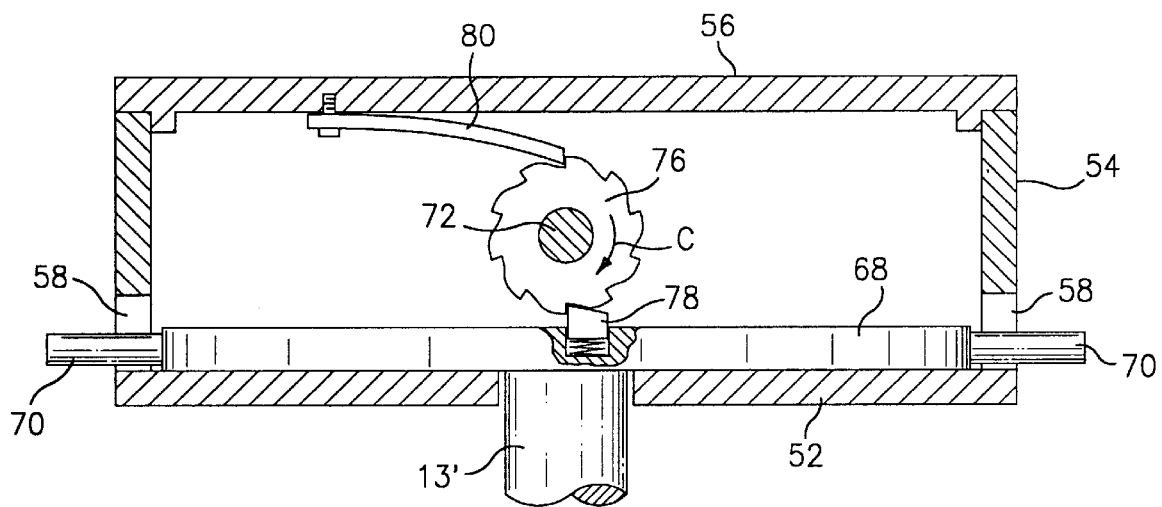
FIG. 7 is a sectional view of the tube rotating mechanism used in performing the method of this invention.

FIGS. 6 and 7 provide details of the manner in which the motor drive shaft 13' is connected to the platen 3; and also details of the manner in which the sample tube 9 is connected to the platen hub 54. The motor drive shaft 13' is affixed to a drive disc 68 which is disposed inside of the hub 54. The disc 68 has a pair of drive pins 70 secured thereto, which drive pins 70 project through the hub windows 58. The drive pins 70 provide the sole driving contact between the motor drive shaft 13' and the platen 3. Rotation of the disc 68 by the motor drive shaft 13' causes the pins 70 to engage the sides of the hub windows 58 thereby causing the hub 54 and the platen 3 to rotate with the disc 68. A rod 72 is rotatably mounted in the hub 54. The rod 72 includes a collar 74 at an end thereof which collar 74 receives one end of the sample tube 9. The collar 74 houses a resilient O-ring (not shown) which grips the end of the tube 9. A toothed ratchet 76 is mounted on the rod 72 and is operable to cause step-wise selective rotation of the collar 74 and sample tube 9 in the following manner. A spring-biased ratchet-engaging pawl 78 is mounted on the disc 68, and a ratchet-engaging blade spring 80 is mounted on the hub cover 56. When the centrifuge motor drive shaft 13' is being powered by the motor 13, rotation of the disc 68 moves the pawl 78 into engagement with one of the teeth on the ratchet 76 and the blade spring 80 moves down into engagement with a diametrically opposed tooth on the ratchet 76, as shown in FIG. 7. In order to selectively rotate the ratchet 76 and sample tube 9, power to the centrifuge motor 13 is periodically interrupted so as to momentarily slow rotation of the drive shaft 13'. The momentum of the platen 3 causes it, and its hub 54, to momentarily rotate at a faster rate than the disc 68 so as to disengage the pawl 78 from the ratchet 76 and to disengage the drive pins 70 from the platen hub 54. During this momentary disengagement, the pawl 78 will disengage from the ratchet tooth, and move to a position wherein it engages the next adjacent ratchet tooth. The motor 13 is then re-energized to full speed, causing the drive pins 70 to re-engage the hub 54 and causing the pawl 78 to impart a clockwise rotation step of the ratchet 76 and the sample tube 9. When the pawl 78 thus drives the next adjacent ratchet tooth, rotation of the ratchet 76 will cause the spring 80 to engage a diametrically opposed next adjacent tooth on the ratchet 76 thus stabilizing the ratchet 76 and the sample tube 9 in the new rotational position. Stepwise rotation of the sample tube 9 thus allows the image dissector 36 to "see" the entire periphery of the sample in the tube 9 as the latter is being centrifuged. Circumferential variations in the position of the descending sample component interfaces 8 will thus be taken into account by the system. The aforesaid pawl and ratchet tube rotating mechanism is the invention of Michael R. Walters of Becton Dickinson and Company, and is described in this application for the purpose of satisfying the "best mode" requirements of the patent statute.

The degree of compaction of material layers in the sample tube can be determined with multiple compaction readings taken while the centrifuge is spinning and the sample tube is being rotated; or can be determined by a sequence of readings taken as the centrifuge continues to spin while the tube is being rotated after a predetermined spin time which is sufficient to fully compact the material layers being measured. In either case, the sample does not have to be transferred from the centrifuge to a separate reading instrument, thus saving time and limiting direct operator contact with the sample. An alternative embodiment of an apparatus which will secure the same readings involves the use of an intense continuous light source, such as a halogen lamp, which will be switched on when a reading is to be taken. In order to achieve a reading speed which is rapid enough to freeze the image of the spinning tube, the electronic shutter on the CCD is opened only for a very short period of time, for example for about one two thousandth of a second when the tube is aligned with the optics. The indexing devices described above can be used to synchronize the opening of the CCD shutter instead of flashing the light source. An advantage of such a system is that a flash tube and its associated circuitry are not required. In order for this second embodiment to operate properly, however, the centrifuge would have to be slowed to about 1,000 RPM in order to produce a clear image of the tube.

Since many changes and variations of the disclosed embodiment of the invention may be made without departing from the inventive concept, it is not intended to limit the invention otherwise than as required by the appended claims.

What is claimed is:

1. A method for determining an ultimate thickness of a gravimetrically compacted layer of a target component in a biological fluid sample, which sample is contained in a transparent tube, said method comprising the steps of:
   a) placing the tube on a centrifuge platen;
   b) spinning the platen so as to commence gravimetric compaction of the target component into a discernable layer in the tube;
   c) performing a plurality of successive preliminary layer thickness readings of the target component while the tube is being centrifuged on the platen, and as the target component continues to form a distinctive layer in the tube;
   d) recording the preliminary layer thickness readings; and
   e) predicting an ultimate thickness of the target component layer from the recorded preliminary layer thickness readings.

2. A method for determining the amount of a target component in an anticoagulated whole blood sample, which blood sample is contained in a transparent tube, said method comprising the steps of:
   a) placing the tube on a centrifuge platen;
   b) spinning the platen so as to commence gravimetric compaction of the target component into a discernable layer in the tube;
   c) performing a plurality of successive preliminary thickness measurements of the target component layer while the tube is being centrifuged on the platen, and as the target component continues to compact into a distinctive layer in the tube;
   d) recording the preliminary layer thickness measurements;
   e) predicting the ultimate thickness of the target component layer from the recorded preliminary layer thickness readings; and
   f) converting said predicted ultimate thickness into a quantification of the amount of the target component in the blood sample.

3. A method for determining an ultimate thickness of a gravimetrically compacted layer of a target component in a biological fluid sample, which sample is contained in a transparent tube, said method comprising the steps of:
   a) placing the tube on a centrifuge platen;
   b) spinning the platen so as to commence gravimetric compaction of the target component into a discernible layer in the tube;
   c) performing a plurality of successive preliminary target component layer thickness readings while the tube is being centrifuged on the platen, and as the target component continues to form a distinctive layer in the tube;
   d) recording the preliminary target component layer thickness readings; and
   e) mathematically predicting an ultimate target component layer thickness from the recorded preliminary target component layer thickness readings.

4. The method of claim 3 further comprising the step of converting said predicted ultimate target component layer thickness into a quantification of the amount of the target component in the biological fluid sample.

5. The method of claim 3 wherein said mathematical predicting step is performed by solving the equation $S=dP/(1/t)$, wherein: S is the slope of change in the target component layer thickness which is derived from said preliminary readings; dP is the change in target component layer thickness which is derived from said preliminary readings; and t is the elapsed time from the start of sample centrifugation to the taking of said preliminary target component layer thickness readings.

6. A method for determining an ultimate thickness of a gravimetrically compacted layer of a target component in a biological fluid sample, which sample is contained in a transparent tube, said method comprising the steps of:
   a) placing the tube on a centrifuge platen;
   b) spinning the platen so as to commence gravimetric compaction of the target component into a discernible layer in the tube;
   c) performing a plurality of successive preliminary target component layer thickness readings while the tube is being centrifuged on the platen, and as the target component continues to form a distinctive layer in the tube; and
   d) mathematically predicting an ultimate target component layer thickness from the preliminary target component layer thickness readings.

7. The method of claim 6 wherein said mathematical predicting step is performed by solving the equation $S=dP/(1/t)$, wherein: S is the slope of change in the target component layer thickness which is derived from said preliminary readings; dP is the change in target component layer thickness which is derived from said preliminary readings; and t is the elapsed time from the start of sample centrifugation to the taking of said preliminary target component layer thickness readings.

8. The method of claim 7 further comprising the step of converting said predicted ultimate target component layer thickness into a quantification of the amount of the target component in the biological fluid sample.

* * * * *